(12) United States Patent
Kura

(10) Patent No.: US 7,951,068 B2
(45) Date of Patent: May 31, 2011

(54) ROTATING SELF-TRAVELING ENDOSCOPE SYSTEM, ROTATING SELF-TRAVELING ENDOSCOPE INSERTION ASSISTING TOOL, AND METHOD FOR TECHNIQUE OF INSERTING ENDOSCOPE INSERTION PORTION INTO SMALL INTESTINE USING ROTATING SELF-TRAVELING ENDOSCOPE SYSTEM

(75) Inventor: Yasuhito Kura, Hachioji (JP)

(73) Assignee: Olympus Medical Systems Corporation, Tokyo (JP)

( * ) Notice: Subject to any disclaimer, the term of this patent is extended or adjusted under 35 U.S.C. 154(b) by 879 days.

(21) Appl. No.: 11/888,069

(22) Filed: Jul. 31, 2007

(65) Prior Publication Data

US 2008/0033245 A1 Feb. 7, 2008

(30) Foreign Application Priority Data

Aug. 3, 2006 (JP) .................... 2006-212557

(51) Int. Cl.
*A61B 1/00* (2006.01)
(52) U.S. Cl. ........ 600/114; 600/115; 600/117; 600/118; 600/137
(58) Field of Classification Search .................. 600/104, 600/106–107, 114–115, 121–123, 137
See application file for complete search history.

(56) References Cited

U.S. PATENT DOCUMENTS

| | | | | |
|---|---|---|---|---|
| 4,934,786 A | * | 6/1990 | Krauter | 385/118 |
| 4,971,033 A | * | 11/1990 | Ehlers | 600/139 |
| 4,998,282 A | * | 3/1991 | Shishido et al. | 381/77 |
| 5,168,864 A | * | 12/1992 | Shockey | 600/144 |
| 5,415,634 A | * | 5/1995 | Glynn et al. | 604/103.08 |
| 5,989,230 A | | 11/1999 | Frassica | |
| 6,783,491 B2 | * | 8/2004 | Saadat et al. | 600/114 |
| 7,029,436 B2 | * | 4/2006 | Iizuka et al. | 600/160 |
| 2004/0186350 A1 | * | 9/2004 | Brenneman et al. | 600/146 |
| 2004/0186368 A1 | * | 9/2004 | Ramzipoor et al. | 600/407 |
| 2006/0100480 A1 | * | 5/2006 | Ewers et al. | 600/114 |
| 2006/0270901 A1 | * | 11/2006 | Bern et al. | 600/114 |

FOREIGN PATENT DOCUMENTS

| | | |
|---|---|---|
| JP | 2000-225092 | 8/2000 |
| JP | 2006-034627 | 2/2006 |

* cited by examiner

*Primary Examiner* — Matthew J Kasztejna
(74) *Attorney, Agent, or Firm* — Scully, Scott, Murphy & Presser, P.C.

(57) ABSTRACT

A rotating self-traveling endoscope system of the invention comprising an insertion portion having an image pickup unit at its distal end portion and a helical structure formed on the outer surface, a rotating driving device for rotating the insertion portion around a long axis, and a rotating self-traveling insertion assisting tool through which the insertion portion can be freely inserted and which is provided with a flexible tube having a bending portion disposed therein is capable of passage of the insertion portion through a space in a body cavity and passage through a valve in the body cavity, which improves insertion performance into a small intestine.

8 Claims, 13 Drawing Sheets

ROTATING SELF-TRAVELING ENDOSCOPE SYSTEM, ROTATING SELF-TRAVELING ENDOSCOPE INSERTION ASSISTING TOOL, AND METHOD FOR TECHNIQUE OF INSERTING ENDOSCOPE INSERTION PORTION INTO SMALL INTESTINE USING ROTATING SELF-TRAVELING ENDOSCOPE SYSTEM

This application claims benefit of Japanese Application No. 2006-212557 filed on Aug. 3, 2006 the contents of which are incorporated by this reference.

BACKGROUND OF THE INVENTION

1. Field of the Invention

The present invention relates to an endoscope which self-travels in a body cavity while rotating around an insertion direction, a self-traveling endoscope system to be externally inserted into an insertion portion of the endoscope for improving insertion performance of the insertion portion into the body cavity and particularly into a small intestine, a rotating self-traveling endoscope insertion assisting tool which assists insertion of the endoscope, and a method for technique of inserting the endoscope insertion portion into the small intestine using the rotating self-traveling endoscope system.

2. Description of the Related Art

Conventionally, a medical endoscope has been used by being inserted into a body cavity for endoscopic inspections. Various proposals have been made for this type of endoscope for easy insertion into a bent lumen such as a colon, which is a body cavity.

Japanese Unexamined Patent Application Publication No. 2006-34627 discloses provision of a helical structure on an outer circumferential surface of an endoscope and a technique for assisting insertion of the endoscope into a body cavity by a thrust by rotation applied by an endoscope insertion assisting device, for example.

Also, Japanese Unexamined Patent Application Publication No. 2000-225092 discloses a self-traveling colon endoscope advance assisting tool which can smoothly insert a self-traveling endoscope into a colon by an anus inserting tube.

SUMMARY OF THE INVENTION

A rotating self-traveling endoscope system of the present invention comprises an insertion portion having an image pickup unit provided at a distal end portion and a helical structure formed on the outer surface, a rotating driving device for rotating the insertion portion around a long axis, and a rotating self-traveling endoscope insertion assisting tool through which the insertion portion can be freely inserted and which is provided with a flexible tube having a bending portion disposed therein.

The rotating self-traveling endoscope assisting tool of the present invention also comprises the bending portion capable of bending at least in two directions, the flexible tube continuously provided at the bending portion and provided with flexibility through which the insertion portion of the rotating self-traveling endoscope can be freely inserted, and an operation portion for bending and operating the bending portion.

Moreover, a first method for technique of inserting the endoscope insertion portion into a small intestine using the rotating self-traveling endoscope system is carried out by using the rotating self-traveling endoscope system provided with an insertion portion having an image pickup unit at the distal end portion and a helical structure formed on the outer surface, a rotating driving device for rotating the insertion portion around a long axis, and a rotating self-traveling endoscope insertion assisting tool through which the insertion portion can be freely inserted and which is provided with a flexible tube with a bending portion disposed, and the distal end portion of the flexible tube is inserted into a duodenum from an oral cavity via a gaster by angle operation of the bending portion, the rotating driving device is driven so as to rotate the insertion portion around the long axis and to generate a thrust by contact between the intestinal wall of the duodenum and the helical structure and the insertion portion is advanced into the deep portion of a small intestine.

Also, a second method for technique of inserting the endoscope insertion portion into the small intestine using the rotating self-traveling endoscope system is carried out by using the rotating self-traveling endoscope system provided with an insertion portion having an image pickup unit at the distal end portion and a helical structure formed on the outer surface, a rotating driving device for rotating the insertion portion around a long axis, and a rotating self-traveling endoscope insertion assisting tool through which the insertion portion can be freely inserted and which is provided with a flexible tube with a bending portion disposed, and the distal end portion is inserted into a colon from an anus, the rotating driving device is driven so as to rotate the insertion portion around the long axis and to generate a thrust by contact between the intestinal wall of the colon and the helical structure, the insertion portion is advanced into the vicinity of a cecum, the distal end portion of the flexible tube is inserted into an ileum by an angle operation of the bending portion so that the Bauhin valve of ileocecum portion is passed, and the rotating driving device is driven again so as to rotate the insertion portion around the long axis and to generate the thrust by contact between the intestinal wall of the ileum and the helical structure so that the insertion portion is advanced into the deep portion of a small intestine.

The above and other objects, features and advantages of the invention will become more clearly understood from the following description referring to the accompanying drawings.

DETAILED DESCRIPTION OF THE PREFERRED EMBODIMENTS

An embodiment of the present invention will be described referring to FIGS. 1 to 22.

Figure 1:
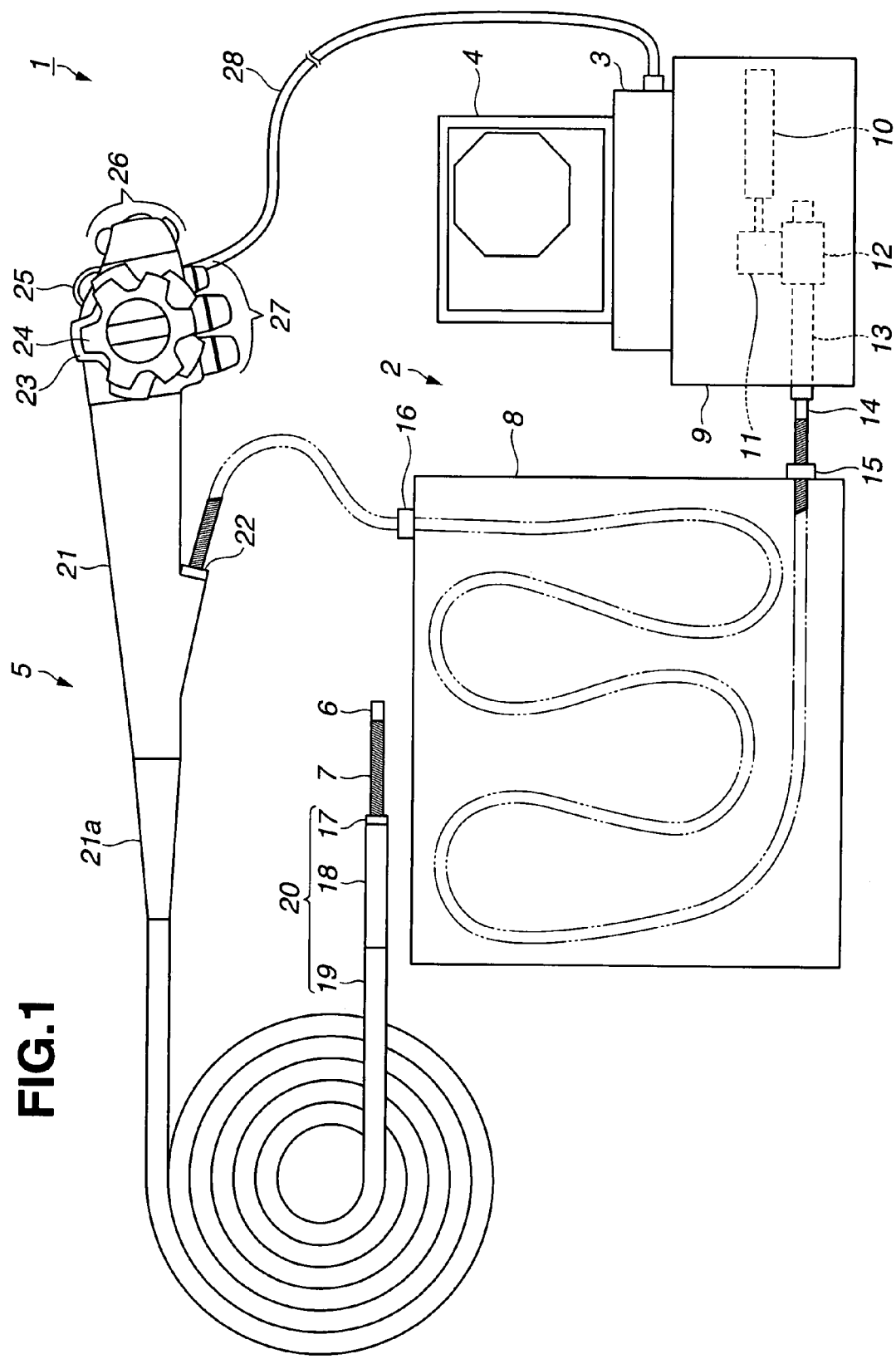
FIG. 1 is an entire block diagram illustrating a rotating self-traveling endoscope system according to an embodiment of the present invention.
Figure 2:
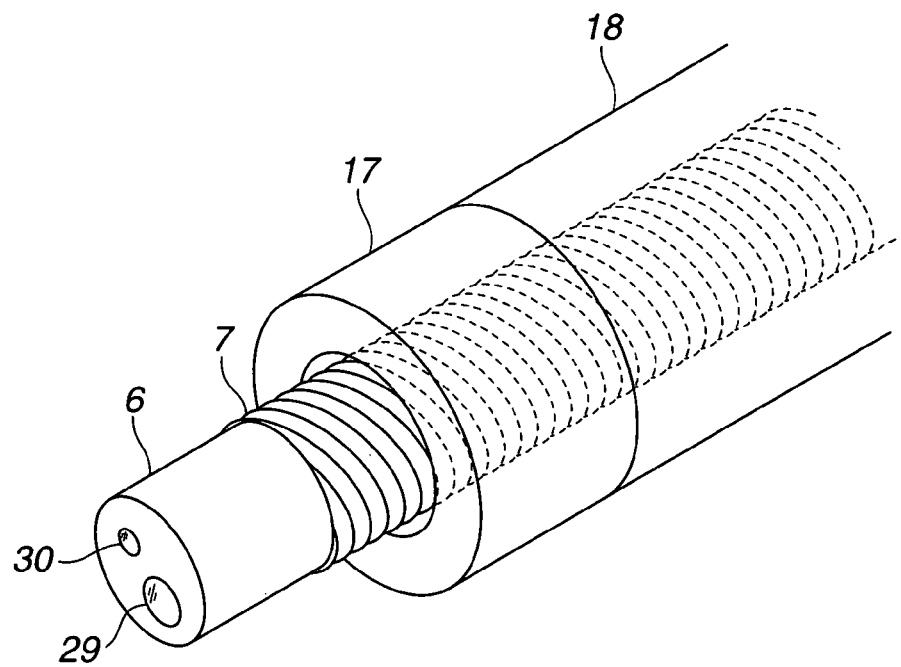
FIG. 2 is a perspective view illustrating a distal end portion of an over tube through which the rotating self-traveling endoscope according to the embodiment of the present invention is inserted.
Figure 3:
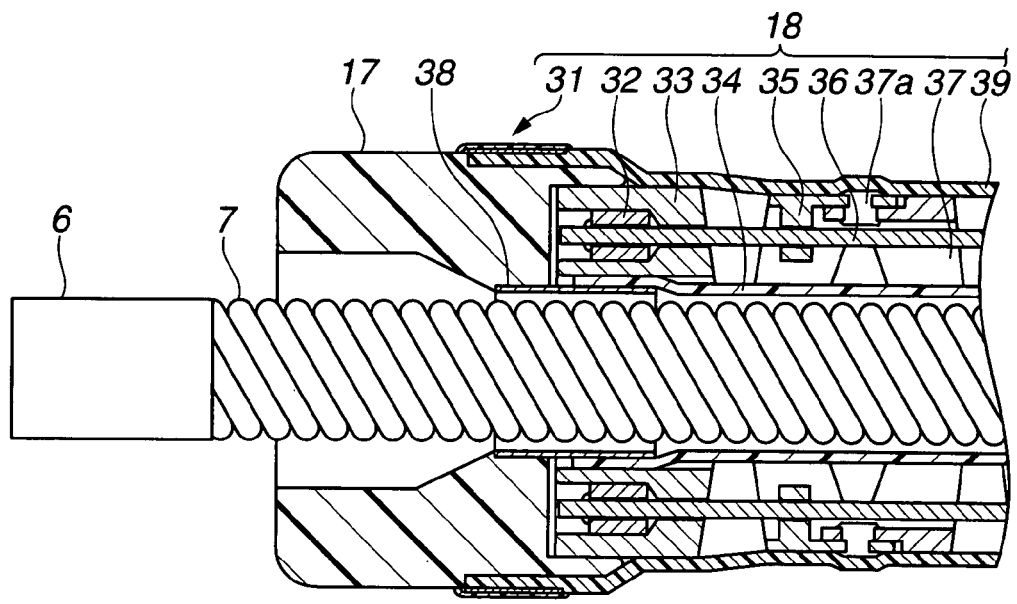
FIG. 3 is a sectional view illustrating the distal end portion of the over tube through which the rotating self-traveling endoscope in the state of FIG. 2 is inserted according to the embodiment of the present invention.
Figure 4:
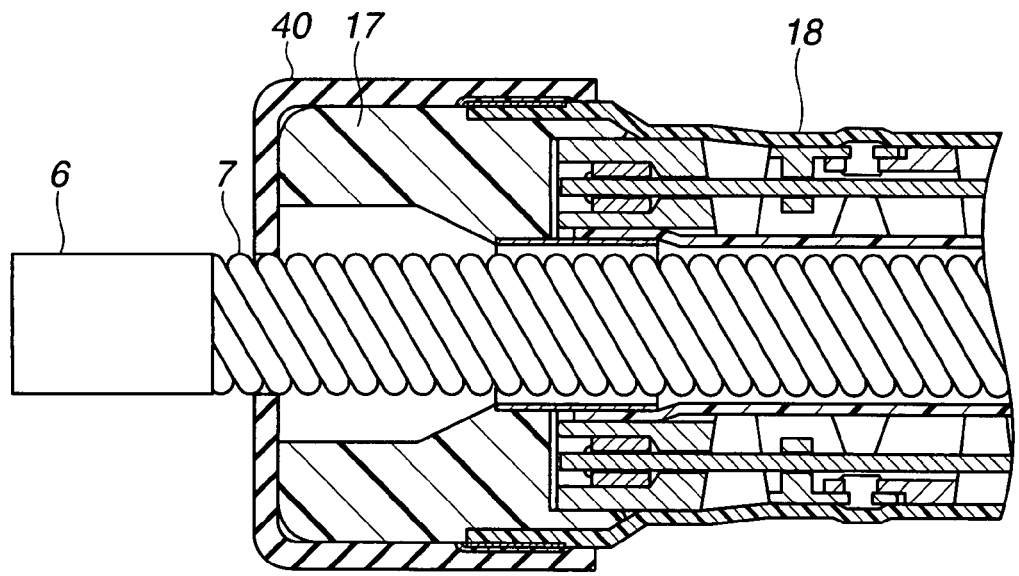
FIG. 4 is a sectional view for explaining a thrust generating cap disposed at the distal end portion of the over tube according to the embodiment of the present invention.
Figure 5:
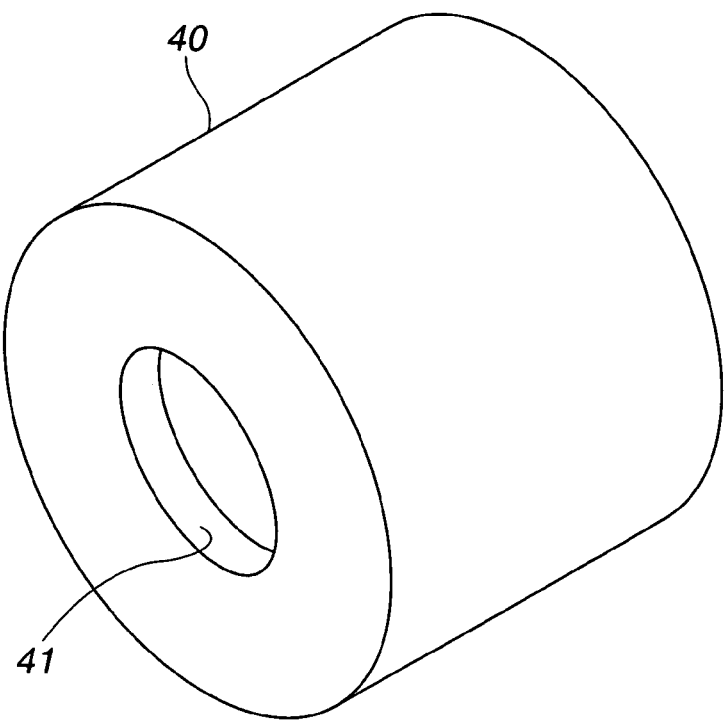
FIG. 5 is a perspective view illustrating the thrust generating cap according to the embodiment of the present invention.
Figure 6:
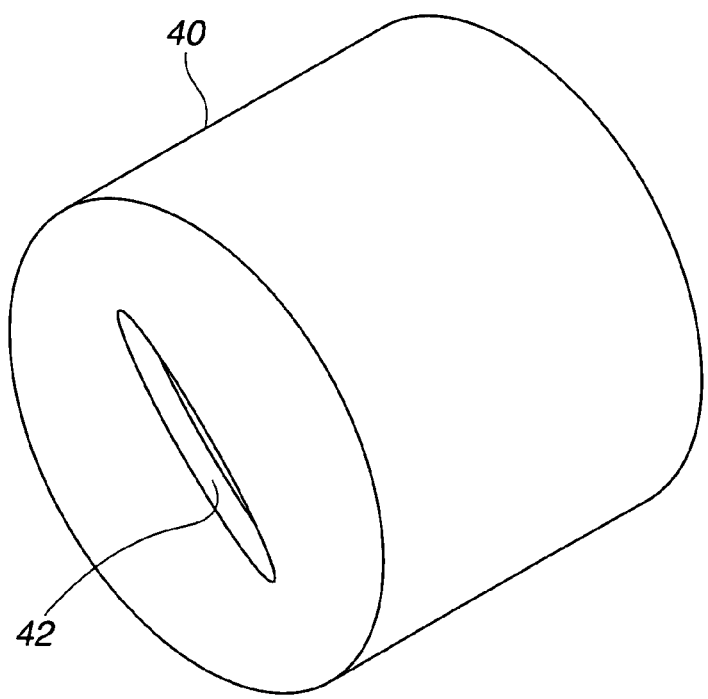
FIG. 6 is a perspective view illustrating the thrust generating cap of a first variation according to the embodiment of the present invention.
Figure 7:
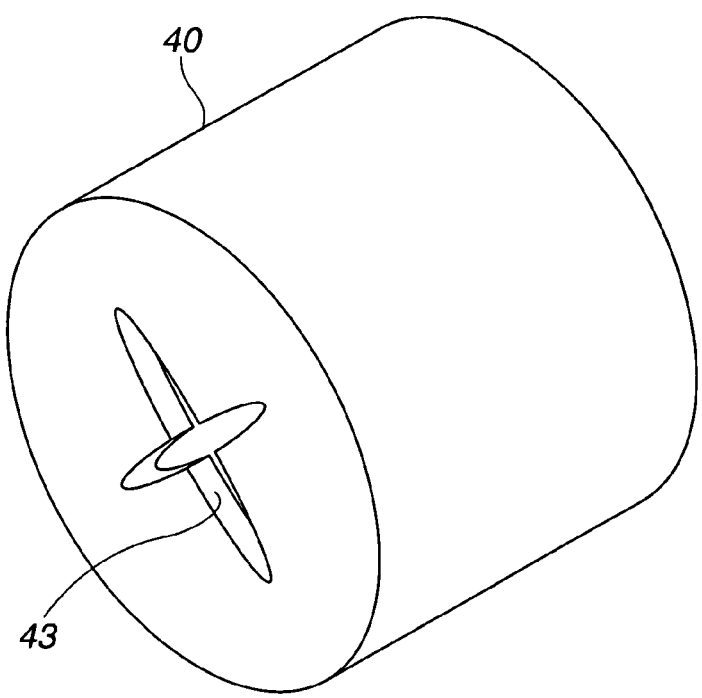
FIG. 7 is a perspective view illustrating the thrust generating cap of a second variation according to the embodiment of the present invention.
Figure 8:
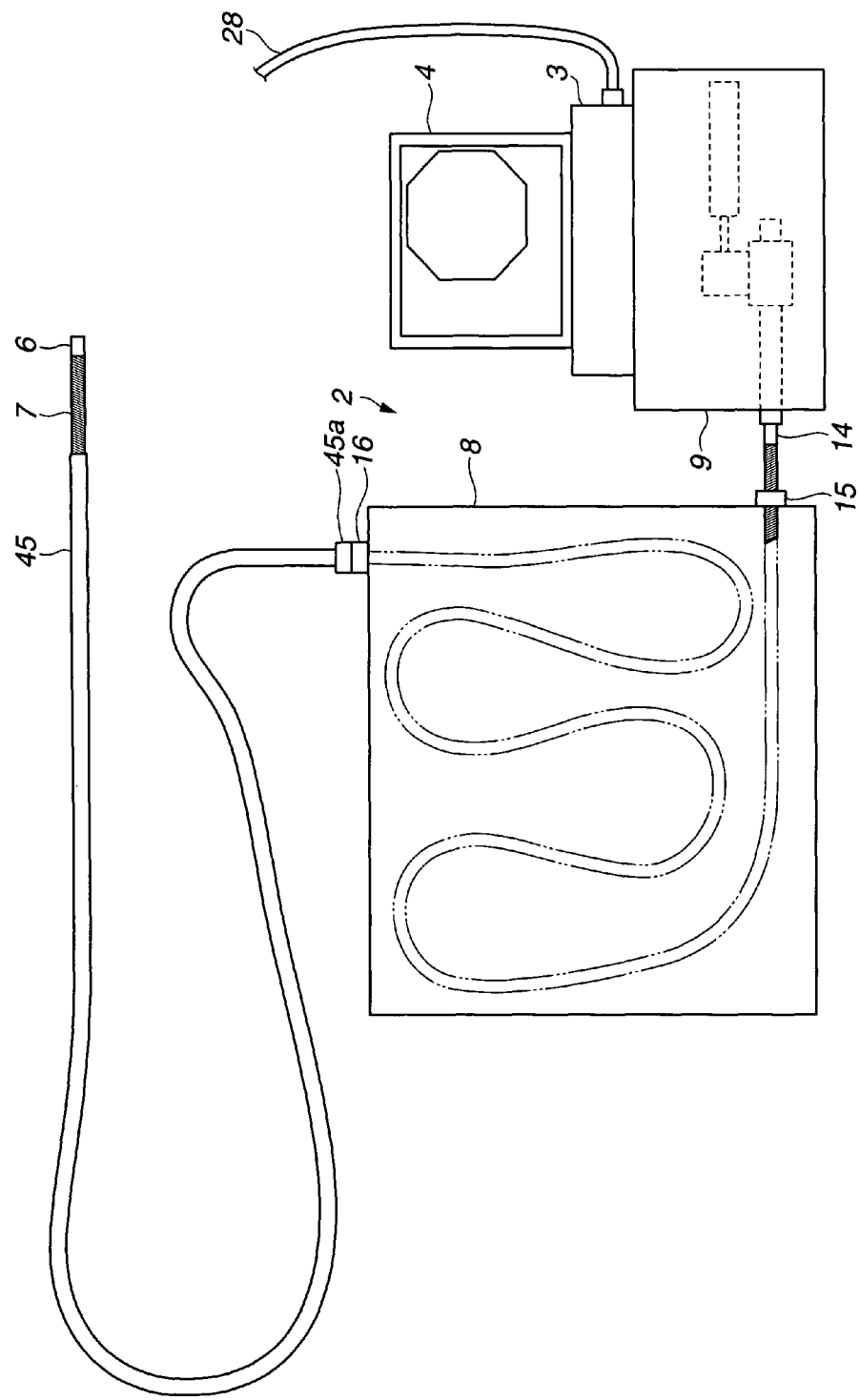
FIG. 8 is an entire block diagram illustrating a rotating self-traveling endoscope showing a variation according to the embodiment of the present invention.
Figure 9:
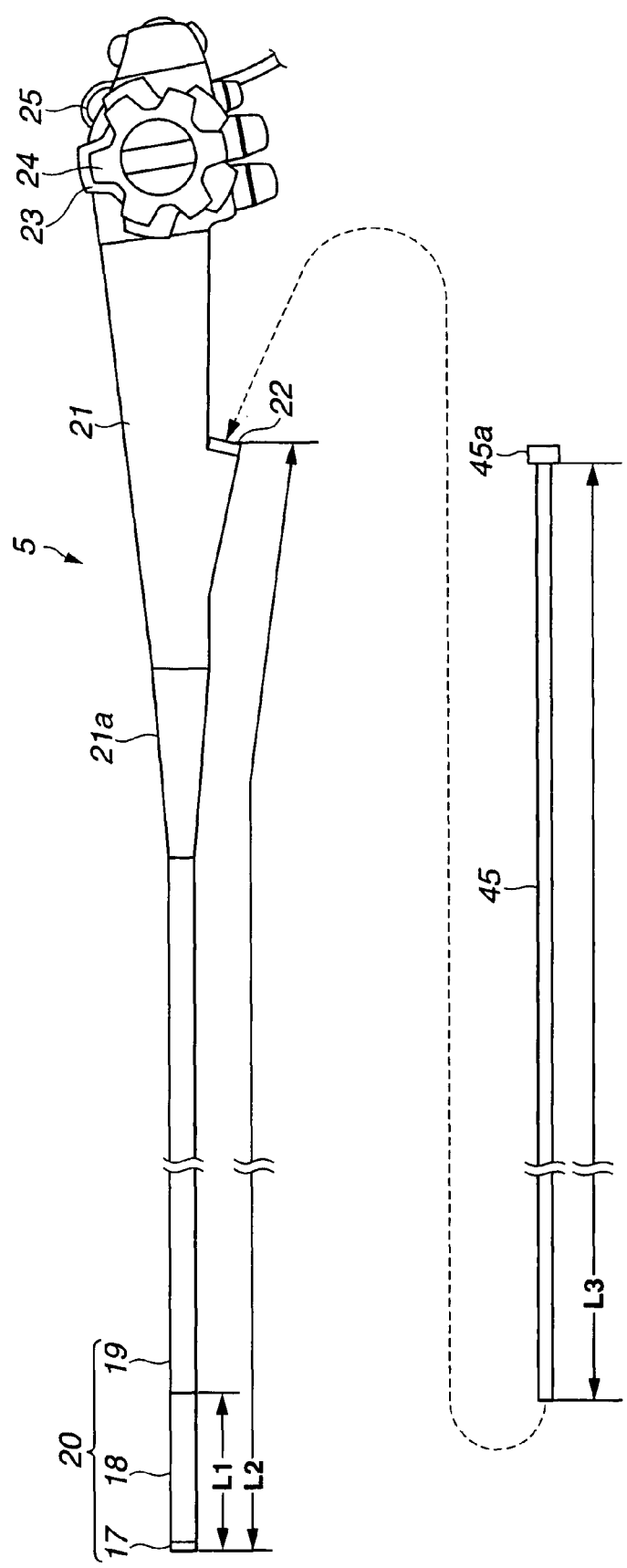
FIG. 9 is a plan view illustrating a length relation between the over tube and a cover tube according to the embodiment of the present invention.

FIGS. 1 to 22 relate to an embodiment of a rotating self-traveling endoscope system and an over tube of the present invention, in which FIG. 1 is an entire block diagram illustrating the rotating self-traveling endoscope system according to the present invention, FIG. 2 is a perspective view illustrating a distal end portion of an over-tube through which the rotating self-traveling endoscope is inserted, FIG. 3 is a sectional view illustrating the distal end portion of the over tube through which the rotating self-traveling endoscope in the state of FIG. 2, FIG. 4 is a sectional view for explaining a thrust generating cap disposed at the distal end portion of the over-tube, FIG. 5 is a perspective view illustrating the thrust generating cap, FIG. 6 is a perspective view illustrating the thrust generating cap of a first variation, FIG. 7 is a perspective view illustrating the thrust generating cap of a second variation, FIG. 8 is an entire block diagram illustrating a rotating self-traveling endoscope showing a variation, FIG. 9 is a plan view illustrating a length relation between the over tube and a cover tube, FIGS. 10 to 16 are views for explaining an example of a technique for inserting the over tube from an oral cavity and the rotating self-traveling endoscope into a small intestine, and FIGS. 17 to 22 are views for explaining an example of a technique for inserting the over tube from an anus and the rotating self-traveling endoscope into the small intestine.

As shown in FIG. 1, the rotating self-traveling endoscope system (hereinafter abbreviated as an endoscope system) 1 mainly comprises a rotating self-traveling endoscope (hereinafter simply abbreviated as an endoscope) 2, a control device 3, which is a camera control unit (CCU), a monitor 4, and an over tube 5, which is a rotating self-traveling endoscope insertion assisting tool.

The endoscope 2 mainly comprises a distal end portion 6, an endoscope insertion portion 7, a housing case 8, and a rotating driving device 9, which is rotating means.

The distal end portion 6 incorporates an image pickup unit, which is image pickup means, not shown, inside. The image pickup unit is provided with an objective optical system 29 and an illumination optical system 30 (See FIG. 2 for both) exposed on the distal end face of the distal end portion 6 and the surface positions are flush with each other. At the position where photographing light incident into the objective optical system 29 is collected, image pickup device (not shown) such as CCD and CMOS are disposed.

An image signal photoelectrically converted by the image pickup device is outputted to a board of the image pickup unit and transmitted to the control device 3 through the rotating driving device 9 via a communication cable inserted through the endoscope insertion portion 7. At the illumination optical system 30, an LED, which is a light source for radiating the illumination light to a subject and is an illuminating member, is provided.

An endoscopic image photographed by the endoscope 2 is image-processed by the control device 3 and displayed on the monitor 4.

The endoscope insertion portion 7 of the present embodiment is a flexible tube body in which a metal wire is helically and closely wound so as to form projections and recesses to be a helical structure in the helical state on the outer circumferential surface. That is, the endoscope insertion portion 7 is a helical tube, considering insertion performance into a body cavity, made of a stainless steel, for example, and a predetermined diameter dimension is set.

The endoscope insertion portion 7 is configured to be rotatable around an axis in the insertion direction. Also, the endoscope insertion portion 7 has its proximal end portion detachable to the rotating driving device 9 by a connector 14. In the endoscope insertion portion 7, the dimension of the projections and recesses to be formed may be changed so as to set a pitch of the projections and recesses and an angle of the helical in various ways.

In the rotating driving device 9, a motor 10 constituting a part of rotating means and a rotating shaft body 13 detachably attached to the endoscope insertion portion 7 by the connector 14 are incorporated. A motor gear 11 of the motor 10 is engaged with a gear 12 of the rotating shaft body 13.

The rotating shaft body 13 is rotated and held at the rotating driving device 9, and a rotating driving force from the motor 10 is transmitted. That is, by the rotating driving force transmitted to the endoscope insertion portion 7, the endoscope insertion portion 7 is rotated around a long axis. And when the endoscope insertion portion 7 is rotated, the helical structure with the projections and recesses on the outer circumferential face is brought into contact with an inner wall of the body cavity of a subject, from which a thrust is generated, and the endoscope insertion portion 7 itself is going to advance in the insertion direction.

The endoscope insertion portion 7 is housed in the housing case 8 between the over tube 5 and the rotating driving device 9. The housing case 8 is a hollow rectangular transparent or translucent case body formed so that a rectangular closed space in the thickness direction slightly larger than the diameter of the endoscope insertion portion 7 is provided.

Opening portions 15, 16 through which the endoscope insertion portion 7 is inserted are disposed on each of two side faces constituting adjacent two sides of the housing case 8. The opening portions 15, 16 are arranged respectively at an end portion in the vicinity of a corner portion on the upper face of the housing case 8 where two side faces are adjacent to each other and an end portion on the side face not located in the vicinity of the opposing corner portion.

In the housing case 8 configured as above, the endoscope insertion portion 7 is inserted from the opening portion 15 as an entrance and guided out of the opening portion 16 as an exit. At this time, the endoscope insertion portion 7 is housed in the meandering state as shown in FIG. 1 within the housing case 8.

In this way, the housing case 8 housing the endoscope insertion portion 7 can be configured so that the rotating lengthy endoscope insertion portion 7 is not overlapped and mingled with each other by twisting, and the endoscope insertion portion 7 can be protected hygienically.

The above-mentioned over tube 5 comprises an insertion portion 20 and an operation portion 21. The insertion portion 20 has a distal-end rigid portion 17 formed by a rigid member, a bending portion 18, and a flexible tube 19 provided with predetermined flexibility formed of a synthetic resin or the like in the order from the distal end. The proximal end of the flexible tube 19 of the insertion portion 20 is connected to a rigid bending stopper portion 21a provided at the operation portion 21 in order to prevent deformation by a rigid member.

In the operation portion 21, an endoscope insertion portion 22 to be an insertion port of the endoscope insertion portion 7 of the endoscope 2 on the side in the middle, two bending operation knobs 23, 24 for bending the bending portion 18 of the insertion portion 20 in four directions (up, down, right and left directions corresponding to an endoscopic image captured by the endoscope 2), a switch lever 25 for driving the rotating driving device 9, switches 27 for various functional operations of the endoscope 2, and switches 26 for operating an optical system such as various photographing and illumination of the endoscope 2 are disposed.

The bending operation knobs 23, 24 are disposed on one side at the proximal end side of the operation portion 21 so that the two knobs in substantially the disk state are overlapped with each other. These two knows are disposed rotatably and constituted by the bending operation knob 23 for U (UP)/D (DOWN) for vertical operation of the bending portion 18 on the side of the operation portion 21 and the bending operation knob 24 for R (RIGHT)/L (LEFT) for horizontal operation of the bending portion 18 on the U/D bending operation knob 23.

In the present embodiment, the bending portion 18 is configured capable of bending in the above four directions but may be configured capable of bending at least in two directions.

From one side face of the operation portion 21, a universal cord 28, which is an electric cord, is extended. At an extended end of the universal cord 28, a connector is disposed, and the connector is detachably connected to the control device 3.

The control device 3 is electrically connected to the rotating driving device 9 and controls the motor 10 on the basis of the operation of the switch lever 25 of the over tube 5.

In the endoscope 2 in the present embodiment, a channel for suction, air/water supply and treatment instrument insertion, not shown, may be disposed at the insertion portion 20. An operation required for the suction and air/water supply of the endoscope 2 can be carried out by switches 27 provided at the operation portion 21 of the over tube 5 in the present embodiment.

For the function of such suction and air/water supply, a water supply tank, an air supply device such as a compressor and a suctioning tool are provided at the control device 3. In the water supply tank, sterilized water is reserved. When the air/water supply button among the switches 27 of the operation portion 21 is given a predetermined operation, the sterilized water is fed by the control device 3 to a water supply tube disposed at the endoscope insertion portion 7 of the endoscope 2 and injected from the distal end portion 6.

At the endoscope insertion portion 7, an air supply tube is disposed, and when a predetermined operation is given to the air/water supply button among the switches 27 of the operation portion 21, air is supplied from a compressor, not shown, in the control device 3, and this air is injected from the distal end portion 6 of the endoscope 2.

When the suction button among the switches 27 is operated, filthy matters are suctioned from the distal end portion 6 of the endoscope 2, and the filthy matters are fed into a suctioning instrument from the control device 3 via a suction tube disposed in the endoscope insertion portion 7. In the rotating self-traveling endoscope 1, the suctioning instrument may be used or a suction system installed at a hospital may be used.

To the control device 3, a foot switch capable of various functional operations of the endoscope 2 may be connected through an electric cable or the like.

Next, the distal end rigid portion 17 and the bending portion 18 constituting a part of the insertion portion 20 of the over tube 5 will be described using FIG. 3.

The distal end rigid portion 17 of the over tube 5 is substantially in the rigid annular state formed by a synthetic resin with biocompatibility and has a connecting ring 38 fitted in an inner circumference portion on the proximal end side.

At the bending portion 18 of the over tube 5, a rigid distal end bending piece 33 fitted at an proximal-end opening portion of the distal end rigid portion 17 and a plurality of rigid bending pieces 37 (also called as bending node rings) are continuously provided rotatably by a pivotally supporting portion 37a. The pieces 33, 37 are covered by a bending outer sheath 39 formed of an elastic member such as a fluoro-rubber with biocompatibility. The distal end portion of the bending outer sheath is fixed to the proximal-end outer circumference portion of the distal end rigid portion 17 by a reel bonding portion 31.

The plurality of bending pieces 37 have a wire guide 35 projecting from the inner circumferential surface toward the center direction. The wire guide 35 has a bending operation wire 36 (also called as an angle wire) inserted therethrough.

There are four bending operation wires 36 in the bending portion 18 (only two of them are shown in FIG. 3), and a cylindrical locking member 32 is fused by solder or the like at the distal end portion of each. In the bending operation wires 36, the respective locking members 32 are locked at four locking hole portions formed at the distal end bending pieces 33.

The four locking hole portions are formed at positions equally divided into four parts with substantially an equal interval on a surface crossing the axis of the distal end bending pieces 33. The positions around the axis of the distal end bending pieces 33 are determined so that each of the locking hole portions is located in correspondence with the up, down, right and left portions of the endoscopic image. Therefore, the four bending operation wires 36 are held and fixed at four points separated with substantially an equal interval in the vertical and horizontal directions.

Also, the bending operation wires 36 are inserted through the insertion portion 20 of the over tube 5 and disposed up to the operation portion 21. Each proximal end portion of the bending operation wires 36 is connected to a bending mechanism portion, not shown, interlocking with the bending operation knobs 23, 24 (See FIG. 1) of the operation portion 21.

Therefore, when each of the four bending operation wires 44 is pulled/loosened by the bending mechanism portion interlocking with the bending operation knobs 23, 24, the plurality of bending pieces 37 are rotated in correspondence. Thus, the bending portion 18 is bent and operated in the above-mentioned four directions.

At the proximal-end outer circumference portion of the connecting ring 38 disposed in the above-mentioned distal end rigid portion 17, the distal end portion of an inner layer tube 34 is fixed. The inner layer tube 34 has its proximal end portion connected to the endoscope insertion portion 22 (See FIG. 1) of the operation portion 21. The flexible tube 19 of the over tube 5 has a coil sheath, not shown, through which each of the above-mentioned bending operation wires 36 is inserted and the above-mentioned inner layer tube 34 inserted.

In the over tube 5 configured as above, the endoscope insertion portion 7 of the endoscope 2 is inserted from the endoscope insertion portion 22 of the operation portion 21, and the distal end portion 6 of the endoscope 2 is made capable of being guided in/out through the opening portion of the distal end rigid portion 17 together with the endoscope insertion portion 7.

As shown in FIG. 4, it may be so configured that a cylindrical cap state thrust generating member formed of an elastic member is constructed at the distal end rigid portion 17 of the over tube 5 and a holding cap 40, which is the thrust generating cap, may be provided.

The holding cap 40 has a hole portion 41 substantially at the center of the distal end face and can be detachably inserted and fixed by its elastic force to the distal end rigid portion 17 of the over tube 5.

The hole portion 41 of the holding cap 40 has its hole diameter set slightly smaller than the outer diameter of the endoscope insertion portion 7 of the endoscope 2. Thus, the holding cap 40 brings the endoscope insertion portion 7 of the endoscope 2 inserted through the hold portion 41 into pressure contact for tightening and assists generation of a thrust by rotation of the endoscope insertion portion 7.

Also, since the endoscope 2 has its distal end portion 6 tightened and fixed by the hole portion 41 of the holding cap 40, it is not displaced at insertion of the over tube 5 into the body cavity. Therefore, a user can insert the over tube 5 into the body cavity while observing an endoscopic image of the endoscope 2.

Such a thrust generating portion assisting generation of a thrust of the endoscope insertion portion 7 may be provided at the endoscope insertion portion 22 of the operation portion 21 of the over tube 5 but may be preferably provided at the distal end portion of the over tube 5 with a high holding and fixing effect of the endoscope 2 and the effect to apply a thrust.

Moreover, in the holding cap 40, instead of the hole portion 41 at the center of the distal end face, a slit 42 as shown in FIG. 6 or a cross slit 43 as shown in FIG. 7 may be provided.

Also, a protective tube 45, which is a protecting member as shown in FIG. 8, may be provided over the endoscope insertion portion 7 of the endoscope 2 of the present embodiment.

More specifically, the protective tube 45 is provided with a connection portion 45a to be detachably or integrally connected to the opening portion 16 as an exit of the endoscope insertion portion 7 of the housing case 8 at one end to be the proximal end side. The protective tube 45 is formed of a flexible tube body rotatably covering the endoscope insertion portion 7 by a predetermined length from the housing case 8.

At the other end portion of the protective tube 45 to be the distal end side, a member assisting generation of a thrust such as the above-mentioned thrust generation portion may be provided at the endoscope insertion portion 7.

The protective tube 45 is inserted from the endoscope insertion portion 22 disposed at the operation portion 21 of the over tube 5 together with the endoscope insertion portion 7 from the operation portion 21 of the over tube 5 to the flexible tube 19.

In order to explain the length relation in the longitudinal direction between the over tube 5 and the protective tube 45, suppose that a length from the distal end (distal end face of the distal end rigid portion 17) of the over tube 5 to the proximal end of the bending portion 18 is L1, a length of the above distal end to the endoscope insertion portion 22 of the operation portion 21 is L2, and a length from the distal end of the protective tube 45 to the connection portion 45a is L3.

At this time, the length L2 from the distal end of the over tube 5 to the endoscope insertion portion 22 of the operation portion 21 is set longer than the length L3 from the distal end of the protective tube 45 to the connection portion 45a (L2>L3). Also, the length L2 is set longer than the length (L1+L3) obtained by adding the length L1 from the distal end of the over tube 5 to the proximal end of the bending portion 18 and the above length L3 together (L2>L1+L3).

By the relation among the above lengths (L1, L2, L3), the protective tube 45 is set so as not to reach inside of the bending portion 18 of the over tube 5. By this, the bending mobility of the bending portion 18 of the over tube 5 is not undermined.

By providing the protective tube 45 covering the endoscope insertion portion 7 in this way, the endoscope 2 can be configured to prevent the inner layer tube 34 in the over tube 5 to be inserted at rotation operation for generating a thrust by the endoscope insertion portion 7 and the endoscope insertion portion 22 of the operation portion 21 from being damaged by the rotation.

Next, two methods of insertion will be described using FIGS. 10 to 22 with regard to a case where the endoscope insertion portion 7 of the rotating self-traveling endoscope system 1 configured as above is approaching a small intestine via a gaster and a case where the small intestine is approached from an anus via a colon.

First, an example of a technique for inserting the endoscope insertion portion 7 of the endoscope 2 from an oral cavity to a small intestine via a gaster by the rotating self-traveling endoscope system 1 of the present embodiment will be described using FIGS. 10 to 16.

Figure 10:
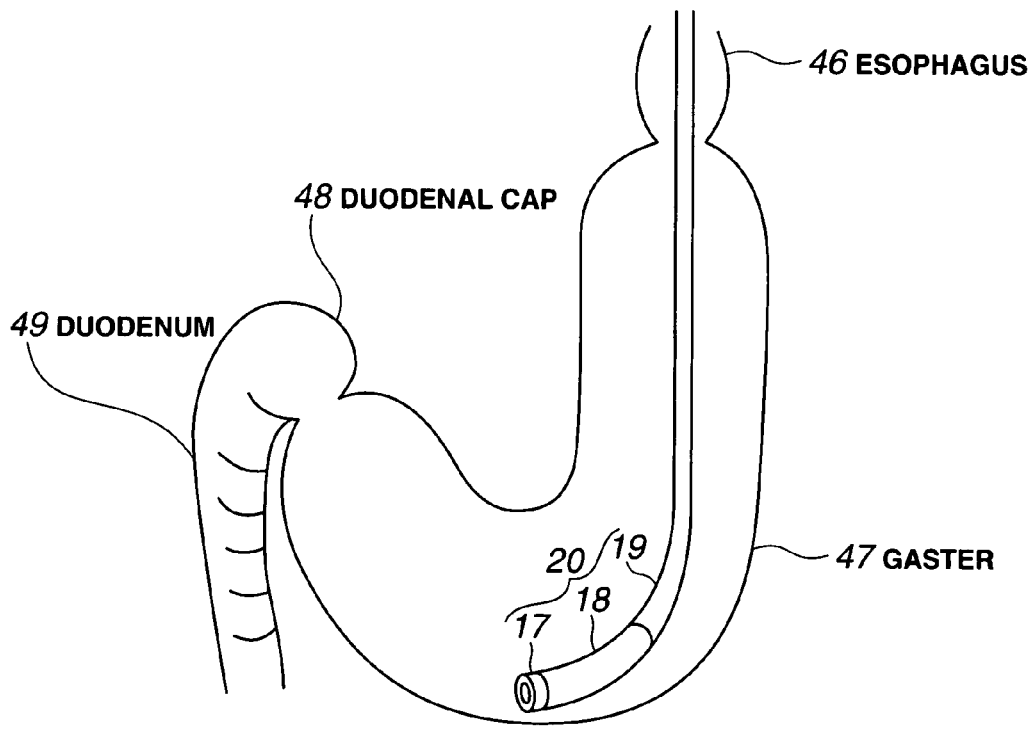
FIG. 10 is a first view for explaining an action showing an example of a technique for inserting the rotating self-traveling endoscope into a small intestine via the over tube according to the embodiment of the present invention from an oral cavity.

First, a user inserts the insertion portion 20 of the over tube 5 from an oral cavity to a gaster via an esophagus 46 and bends the bending portion 18 in the upper (UP) angle direction by the U/D bending operation knob 23 of the operation portion 21 as shown in FIG. 10. At this time, the endoscope insertion portion 7 of the endoscope 2 has been inserted into the insertion portion 20 of the over tube 5 in advance. When these operations are to be carried out, the user performs the insertion operation of the insertion portion 20 while observing an endoscopic image by locating the distal end portion 6 of the endoscope 2 at the distal end rigid portion 17 of the over tube 5.

Figure 11:
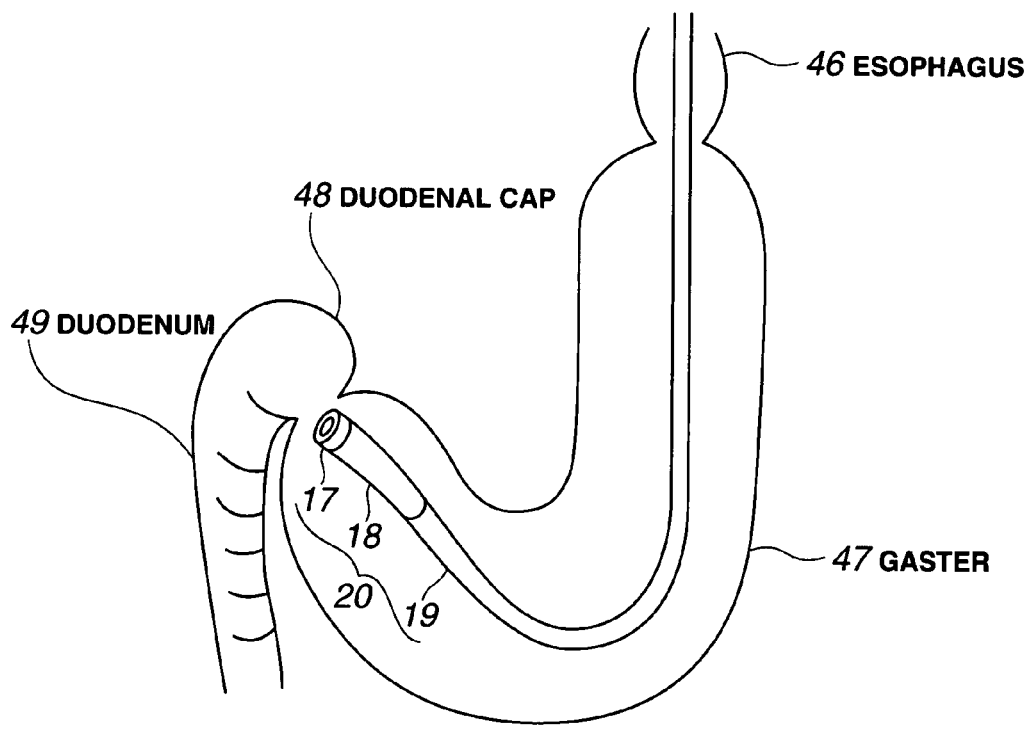
FIG. 11 is a second view for explaining an action showing an example of a technique for inserting the rotating self-traveling endoscope into a small intestine via the over tube according to the embodiment of the present invention from an oral cavity.

Next, the user pushes in the insertion portion 20 by repeatedly performing an angle operation of the bending portion 18 vertically and horizontally by the bending operation knobs 23, 24 of the operation portion 21 so that the distal end rigid portion 17 reaches the pyloric ring, which is an entrance to a duodenal cap 48, as shown in FIG. 11. During passage from the pyloric ring to the duodenal cap 48, the user makes the angle of the bending portion 18 neutral.

Figure 12:
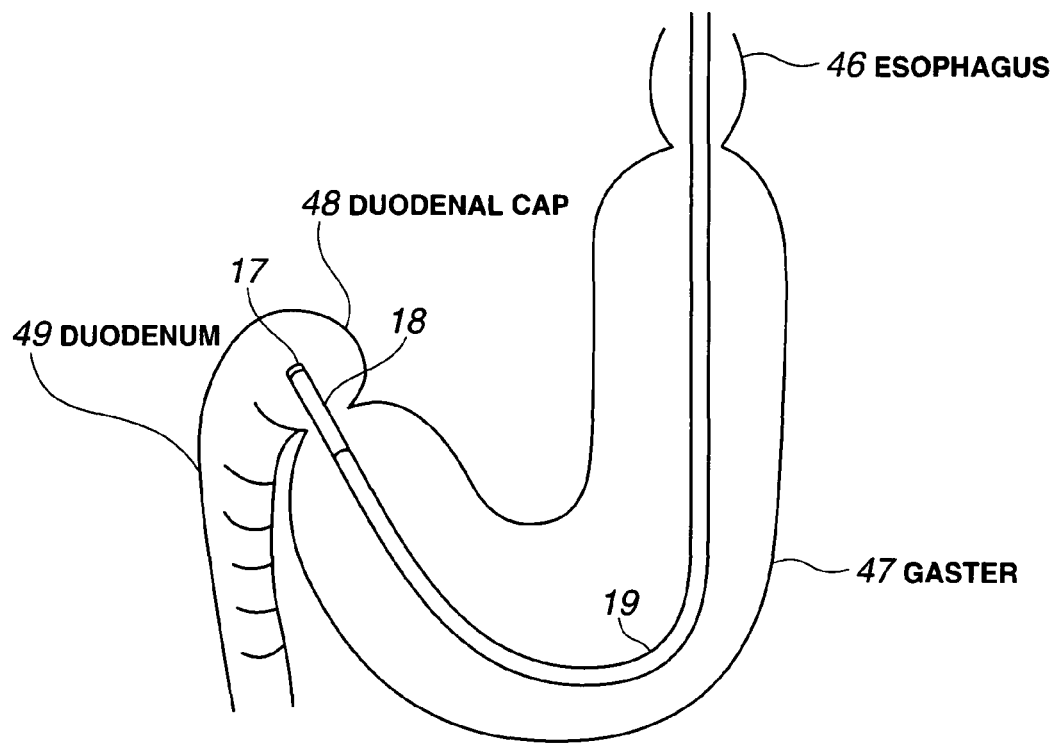
FIG. 12 is a third view for explaining an action showing an example of a technique for inserting the rotating self-traveling endoscope into a small intestine via the over tube according to the embodiment of the present invention from an oral cavity.
Figure 13:
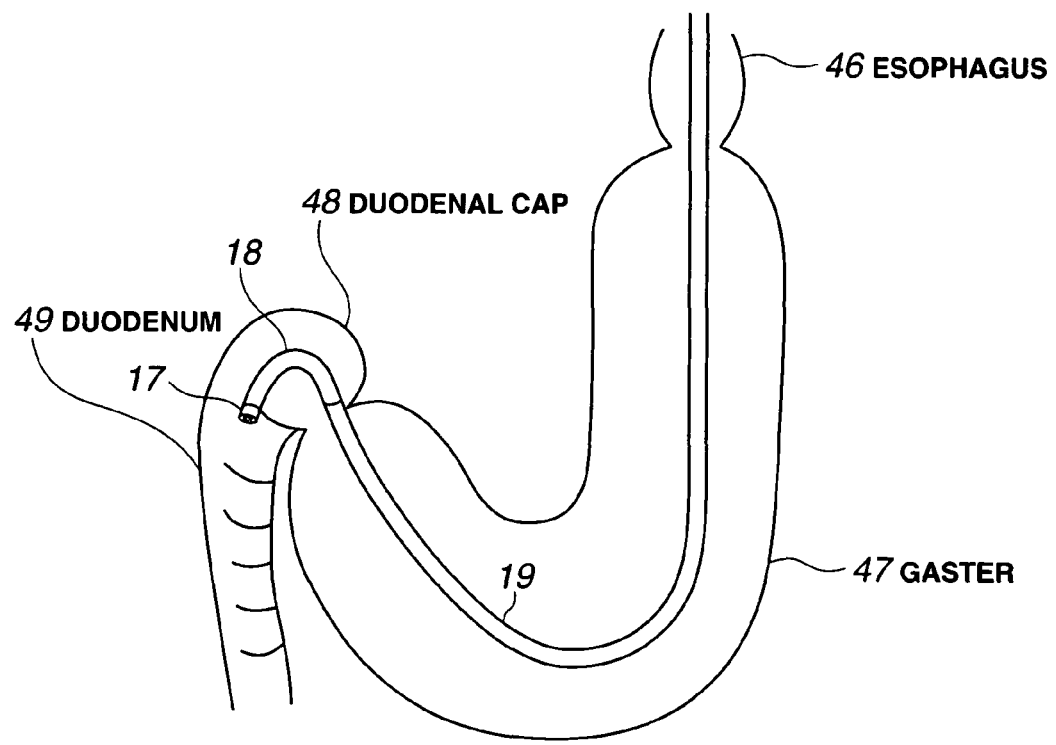
FIG. 13 is a fourth view for explaining an action showing an example of a technique for inserting the rotating self-traveling endoscope into a small intestine via the over tube according to the embodiment of the present invention from an oral cavity.

And when the distal end rigid portion 17 of the insertion portion 20 reaches the duodenal cap 48 as shown in FIG. 12, the user operates the bending operation knobs 23, 24 of the operation portion 21 while pushing in the insertion portion 20 so as to give an angle to the bending portion 18 toward the descending leg of a duodenum 49 as shown in FIG. 13.

Figure 14:
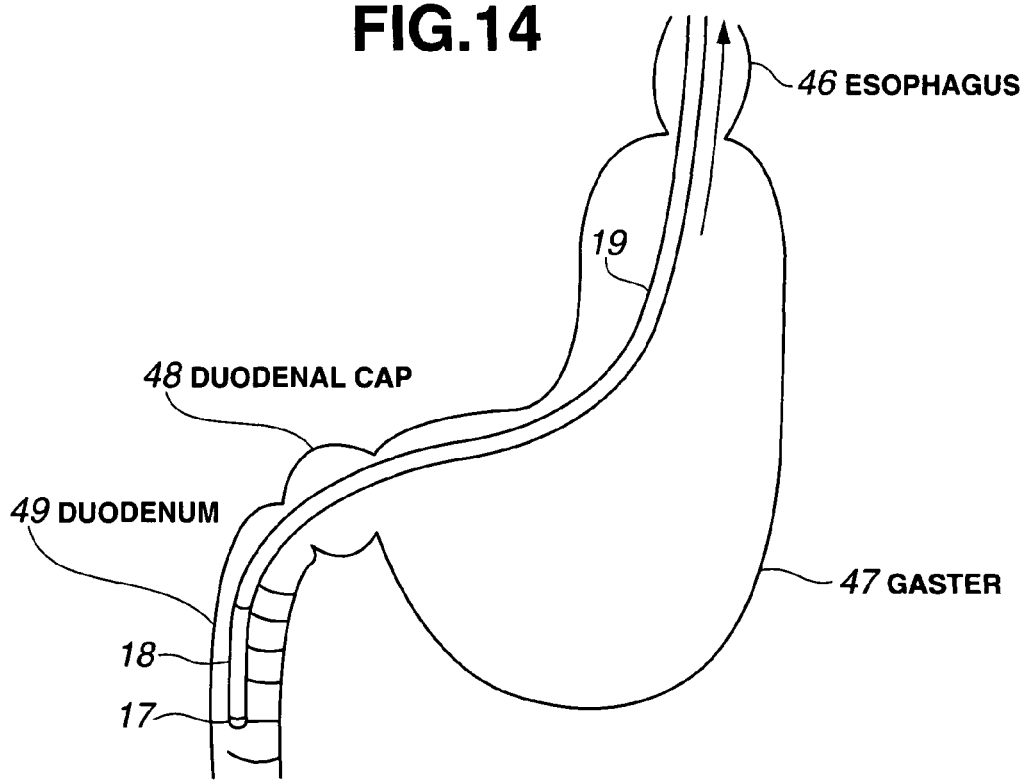
FIG. 14 is a fifth view for explaining an action showing an example of a technique for inserting the rotating self-traveling endoscope into a small intestine via the over tube according to the embodiment of the present invention from an oral cavity.
Figure 15:
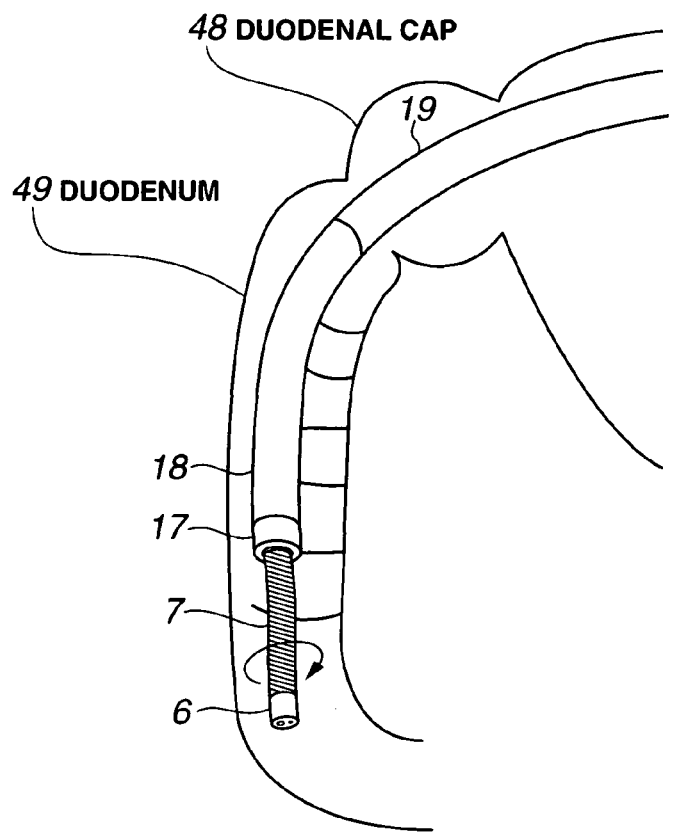
FIG. 15 is a sixth view for explaining an action showing an example of a technique for inserting the rotating self-traveling endoscope into a small intestine via the over tube according to the embodiment of the present invention from an oral cavity.

Next, when the user pulls the insertion portion 20 of the over tube 5 while performing a twisting operation as shown in FIG. 14, the insertion portion 20 is made straight. After that, the user rotates the insertion portion 7 of the endoscope 2 in a predetermined direction as shown in FIG. 15 by operating the switch lever 25 of the operation portion 21 while the distal end side of the over tube 5 is inserted into the duodenum 49.

Figure 16:
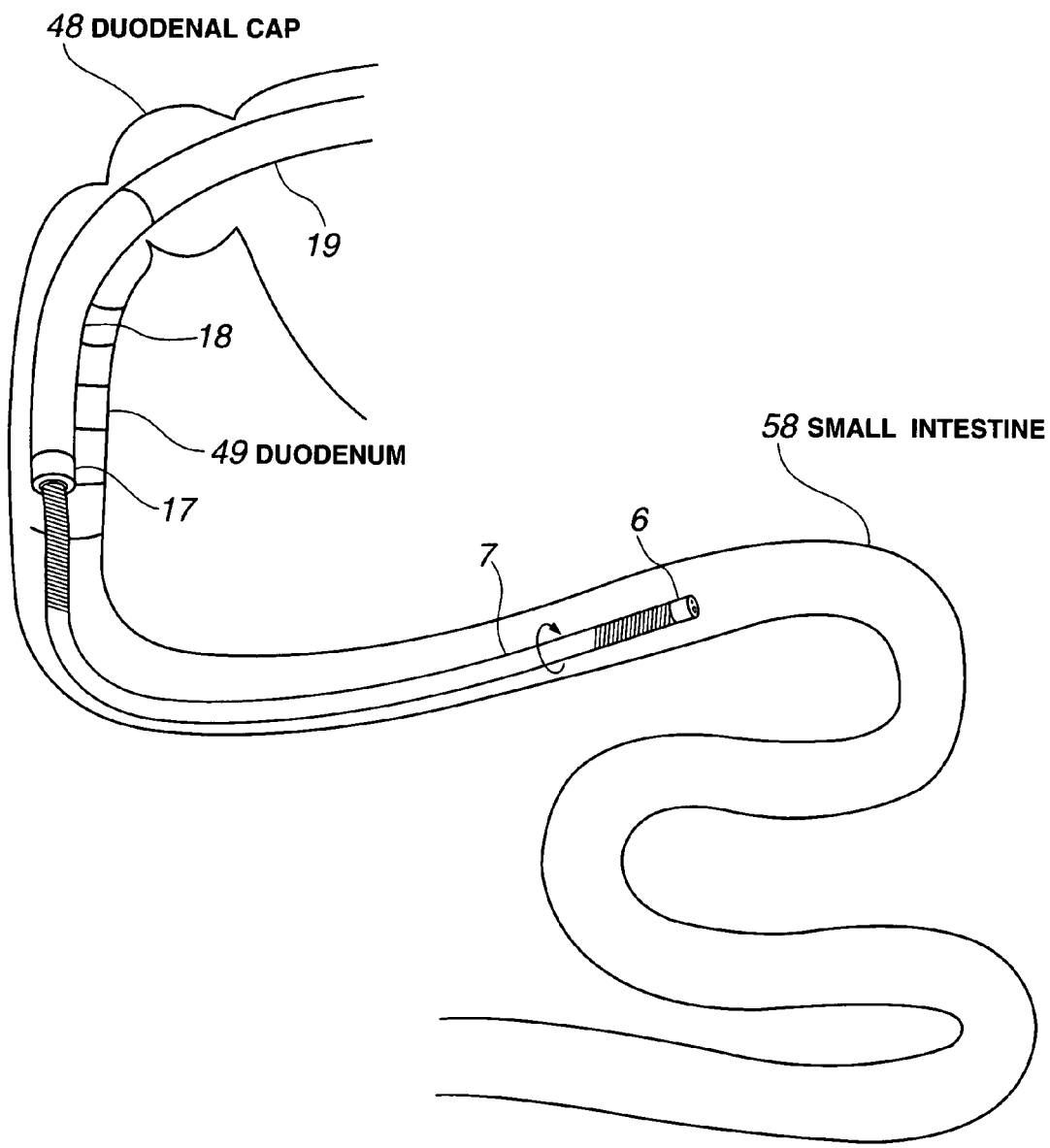
FIG. 16 is a seventh view for explaining an action showing an example of a technique for inserting the rotating self-traveling endoscope into a small intestine via the over tube according to the embodiment of the present invention from an oral cavity.
Figure 17:
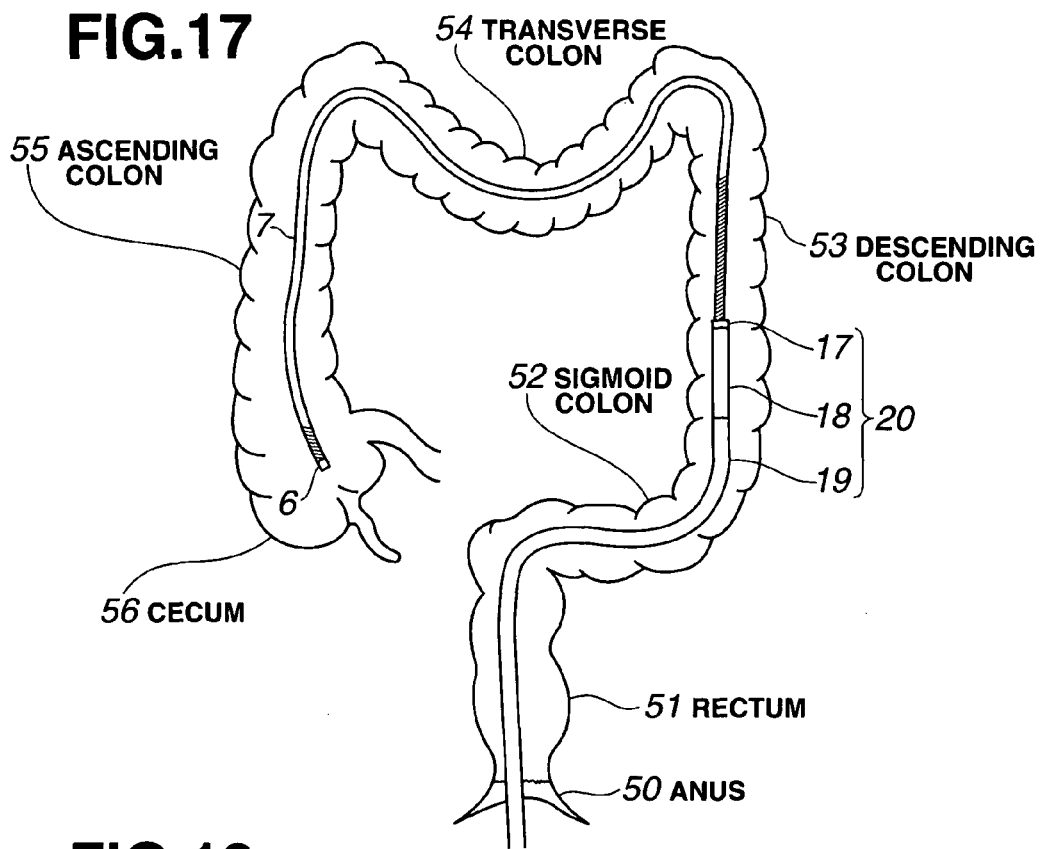
FIG. 17 is a first view for explaining an action showing an example of a technique for inserting the rotating self-traveling endoscope into a small intestine via the over tube according to the embodiment of the present invention from an anus.

In this way, the endoscope insertion portion 7 of the endoscope 2 self-travels by generation of a thrust through contact between a helical structure formed on the outer circumference portion and an intestinal wall of the duodenum 48 and advances in the direction of a deep portion of the small intestine 58 as shown in FIG. 16. Moreover, the user can advance the distal end portion 6 of the endoscope 2 into the deep portion of the small intestine 58 by keeping on rotating the endoscope insertion portion 7.

Also, the user can retreat the endoscope insertion portion 7 in the removal direction by reversing the rotating direction of the endoscope insertion portion 7 inserted into the direction of the deep portion of the small intestine 58 by operation of the switch lever 25.

As having been described above, according to the rotating self-traveling endoscope system 1 of the present embodiment, since the rotating endoscope insertion portion 7 does not directly touch organs from the throat of a patient to the esophagus 46 and the gaster 47 by the insertion portion 20 of the over tube 5 at insertion of the endoscope insertion portion 7 from the oral cavity, a pain (burden) of the patient can be reduced.

Also, by this technique, the rotating self-traveling endoscope system 1 can pass the insertion portion 20 of the over tube 5 through the gaster 47 having a large space and guide the endoscope insertion portion 7 of the endoscope 2 to the duodenum 49. Therefore, the user can easily insert the endoscope insertion portion 7 to the deep portion of the small intestine 58 through self-traveling by propelling action of the helical structure formed on the outer circumference portion of the endoscope insertion portion 7 by rotation on the intestinal wall of the duodenum 49 and the small intestine 58 ahead of the duodenum.

Next, an example of the technique to insert the endoscope insertion portion 7 of the endoscope 2 from an anus to the small intestine via a colon by the rotating self-traveling endoscope system 1 of the present embodiment will be described using FIGS. 17 to 22.

First, the user rotates the endoscope insertion portion 7 of the endoscope 2 in a predetermined direction and passes the insertion portion by propelling self-traveling generated by contact between an intestinal wall of an anus 50 of a colon to a rectum 51, a sigmoid colon 52, a descending colon 53, a transverse colon 54, and an ascending colon 55 and the helical structure formed on the outer circumference portion of the endoscope insertion portion 7 so as to insert the distal end portion 6 into the vicinity of a cecum 56.

Figure 18:
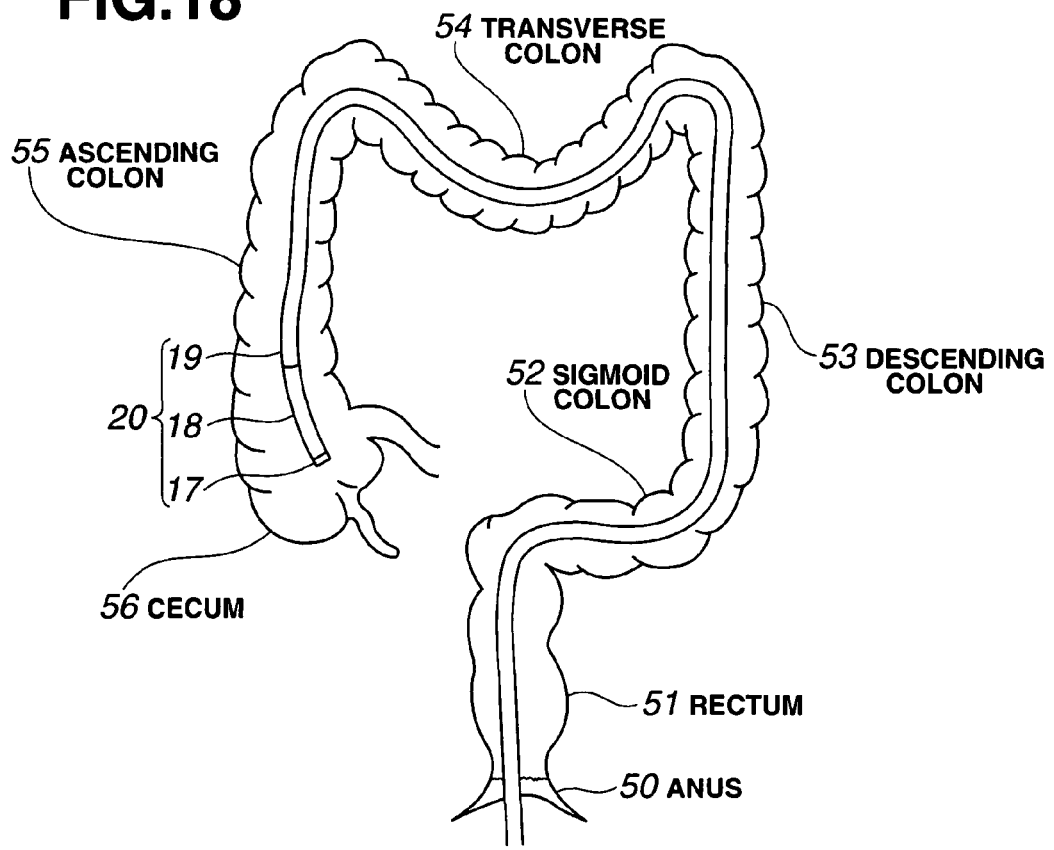
FIG. 18 is a second view for explaining an action showing an example of a technique for inserting the rotating self-traveling endoscope into a small intestine via the over tube according to the embodiment of the present invention from an anus.
Figure 19:
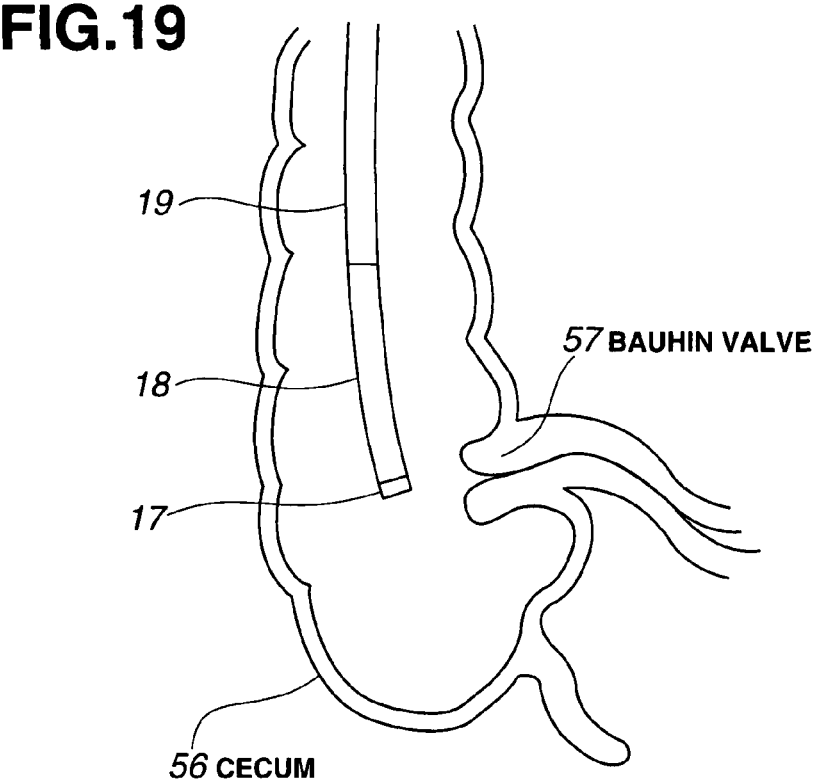
FIG. 19 is a third view for explaining an action showing an example of a technique for inserting the rotating self-traveling endoscope into a small intestine via the over tube according to the embodiment of the present invention from an anus.
Figure 20:
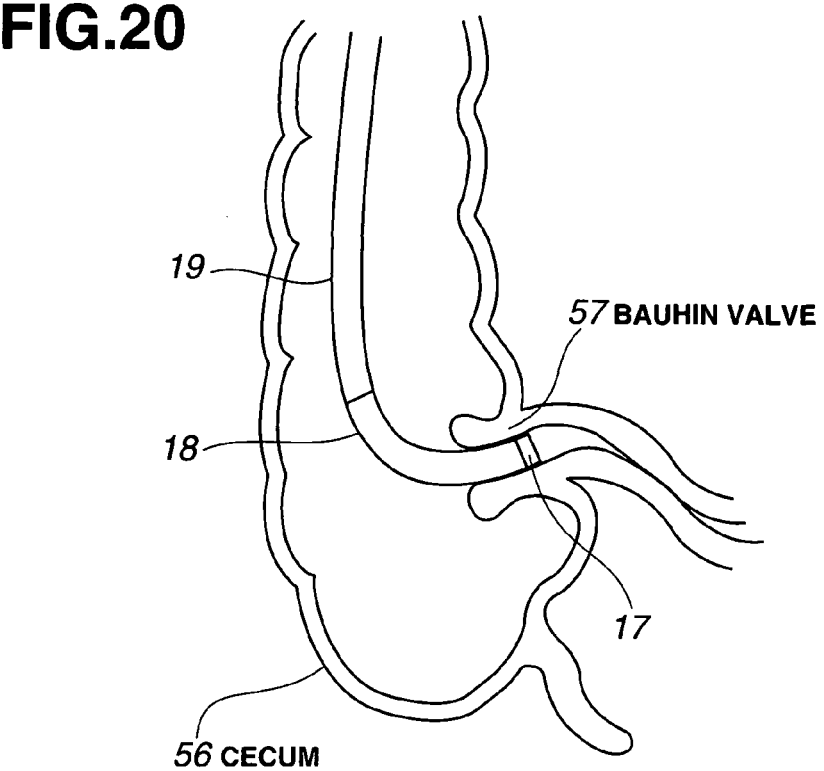
FIG. 20 is a fourth view for explaining an action showing an example of a technique for inserting the rotating self-traveling endoscope into a small intestine via the over tube according to the embodiment of the present invention from an anus.

Then, the user inserts the insertion portion 20 of the over tube 5 along the endoscope insertion portion 7 to the vicinity of the cecum 56 as shown in FIG. 18. After that, the user inserts the distal end rigid portion 17 of the over tube 5 so as to pass the Bauhin valve 57 by angle operation of the bending portion 18 of the over tube 5 through the bending operation knobs 23, 24 of the operation portion 21 as shown in FIG. 20 from the state in FIG. 19 while observing the position of the Bauhin valve 57 of an ileocecum portion.

Then, the user surely inserts the distal end rigid portion 17 into an ileum on the side of the small intestine 58 so as to pass the Bauhin valve 57 by slightly returning the angle of the bending portion 18 through the bending operation knobs 23, 24 of the operation portion 21.

Figure 21:
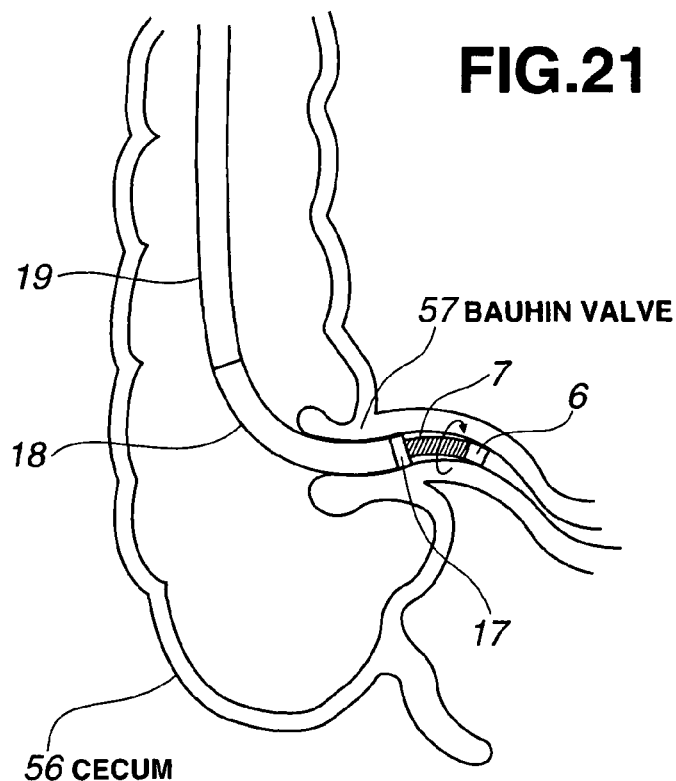
FIG. 21 is a fifth view for explaining an action showing an example of a technique for inserting the rotating self-traveling endoscope into a small intestine via the over tube according to the embodiment of the present invention from an anus.

After that, the user rotates the insertion portion 7 of the endoscope 2 in a predetermined direction as shown in FIG. 21 by operation of the switch lever 25 of the operation portion 21 while the distal end side of the over tube 5 is inserted in the Bauhin valve 57.

Figure 22:
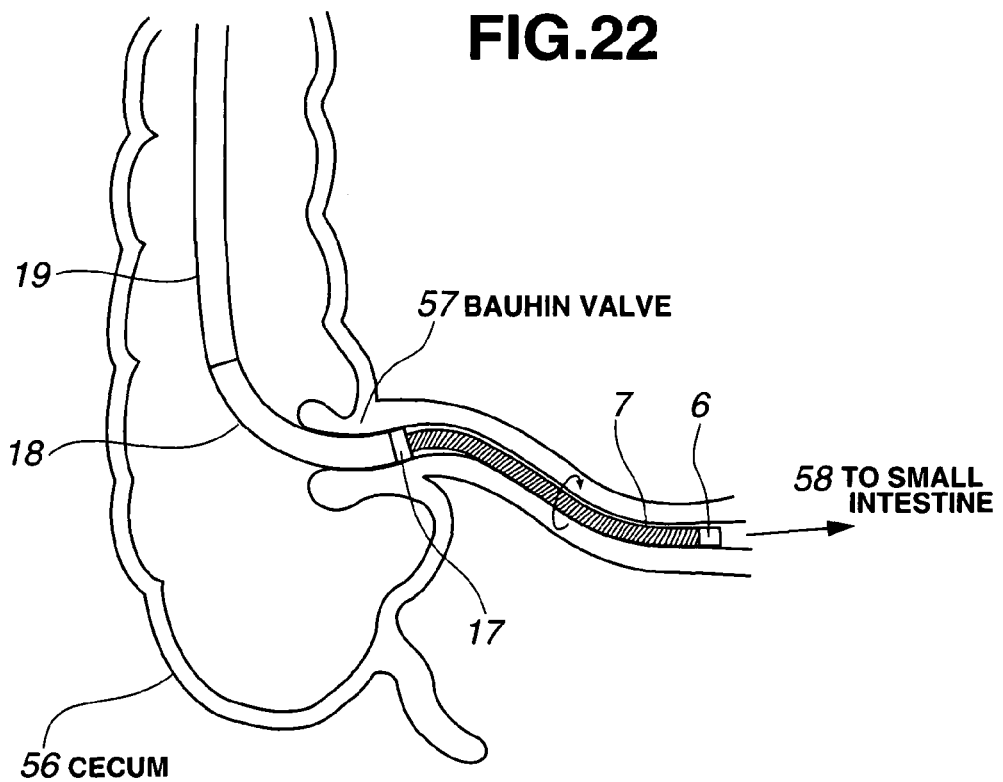
FIG. 22 is a sixth view for explaining an action showing an example of a technique for inserting the rotating self-traveling endoscope into a small intestine via the over tube according to the embodiment of the present invention from an anus.

By bring the helical structure formed on the outer circumference portion in contact with the intestinal wall of the small intestine 58 in this way, the endoscope insertion portion 7 of the endoscope 2 self-travels by generation of a thrust and advances in the direction of the deep portion of the small intestine 58 as shown in FIG. 22. Moreover, the user can advance the distal end portion 6 of the endoscope 2 into the deep portion of the small intestine 58 by keeping on rotating the endoscope insertion portion 7.

Also, the user can retreat the endoscope insertion portion 7 in the removal direction by reversing the rotating direction of the endoscope insertion portion 7 inserted in the direction of the deep portion of the small intestine 58 by operation of the switch lever 25 of the operation portion 21.

As described above, according to the rotating self-traveling endoscope system 1 of the present embodiment, at insertion of the endoscope insertion portion 7 from the anus 50 to the deep portion of the small intestine 58 via the colon, the endoscope insertion portion 7 can be easily passed through the Bauhin valve 57 at the closed ileocecum portion to be a boundary portion between the ileum and the colon as an exit of the small intestine, insertion through which has been considered difficult.

As a result, the rotating self-traveling endoscope system 1 of the present embodiment enables easy passage of the endoscope insertion portion 7 propelling and self-traveling by rotation through a space of a body cavity such as the gaster 47 and the Bauhin valve 57 of the ileocecum portion and can improve insertion performance into the small intestine 58, insertion through which has been thought to be difficult, whether the approach is from the oral cavity or the anus.

That is, in an endoscopic inspection, the flexible insertion portion of the endoscope should be inserted through a long and winding colon or a deep portion of a small intestine, and a skilled technique is required for doctors. Particularly, the small intestine exceeds 6 m in length and occupies approximately 80% of the digestive tract and the small intestine is an important organ for digestion and absorption. Therefore, for the small intestine, early discovery of abnormality in an internal tissue is important. The approach of the endoscope into the small intestine has a case of insertion from the oral cavity via the gaster and a case of insertion from the anus via the colon.

Then, the rotating self-traveling endoscope system 1 of the present embodiment is capable of approach to the small intestine from the oral cavity via the gaster, which has not been possible with the conventional endoscope with the rotating insertion portion. Also, the rotating self-traveling endoscope system 1 of the present embodiment is configured to self-travel in contact beyond the gaster to the entrance to the small intestine and further to the intestinal wall of the duodenum at the deeper portion, not requiring contact between the helical structure of the endoscope insertion portion 7 and the gastric wall in the gaster having a large space.

Also, the user as a doctor can easily pass the endoscope distal end portion 6 through the Bauhin valve of the closed ileocecum portion to be the exit of the small intestine and the boundary portion between the ileum and the colon in the case of an approach of the endoscope insertion portion 7 from the colon, using the rotating self-traveling endoscope system 1 of the present embodiment.

Moreover, the endoscope insertion portion 7 of the present embodiment should have some body to pass through a wide space such as a gaster but does not have to rely on its own rigidity in the gaster and is configured to have flexibility for self-traveling propelling in the small intestine.

As described above, a rotating self-traveling endoscope system in which the flexible endoscope insertion portion 7 which propels and self-travels by rotation can easily pass the space in the body cavity and a valve in the lumen, and a rotating self-traveling endoscope insertion assisting tool and a method of technique for inserting the endoscope insertion portion into the small intestine by the rotating self-traveling endoscope system can be realized particularly with an excellent insertion performance into the small intestine.

The above described invention is not limited to each of the embodiments but various variations can be put into practice in a range not departing from its gist. Moreover, in each of the embodiment, inventions at various stages are included and various inventions can be extracted by appropriate combination in a plurality of disclosed constituent features.

For example, even if some constituent features are deleted from all the constituent features shown in each embodiment, the configuration after the deletion of the constituent features can be extracted as the invention, provided that the problem stated in the problems to be solved by the invention can be obtained.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A rotating self-traveling endoscope system comprising:
    an insertion portion having an image pickup unit provided at a distal end portion of the insertion portion and a helical structure formed on an outer surface of the insertion portion, the insertion portion being configured to rotatably advance in a longitudinal axis direction thereof;
    a rotating driving device for rotating the insertion portion around the longitudinal axis thereof;
    a flexible tube having a lumen through which the insertion portion is rotatably advanced;
    a bending portion disposed continuously at a distal end side of the flexible tube, the bending portion being configured to bend in an instructed direction; and
    a protecting member having flexibility and inserted through the lumen of the flexible tube, for separating the helical structure of the insertion portion from an inner surface of the flexible tube,
    wherein the protecting member has an entire length not reaching the bending portion in a state of being inserted through the lumen of the flexible tube so as to prevent a bending mobility of the bending portion from being undermined.

2. The rotating self-traveling endoscope system according to claim 1, wherein
    the flexible tube is provided with a thrust generating member which is capable of detachable attachment, holds the helical structure of the insertion portion in pressure contact and generates a thrust.

3. The rotating self-traveling endoscope system according to claim 2, further comprising
    a protecting member covering the insertion portion and inserted through the flexible tube together with the insertion portion.

4. The rotating self-traveling endoscope system according to claim 3, wherein
    the protecting member has a length not reaching inside of the bending portion in the state inserted through the flexible tube.

5. The rotating self-traveling endoscope system according to claim 1, further comprising:
    a distal-end rigid portion disposed continuously at a distal end side of the bending portion and having a distal end opening from which the insertion portion is guided out; and
    a thrust generating member provided at the distal-end rigid portion, the thrust generating member being in pressure contact with the helical structure to assist advancement and retreat of the insertion portion.

6. The rotating self-traveling endoscope system according to claim 1, further comprising a thrust generating member provided at the protecting member, the thrust generating member being in pressure contact with the helical structure to assist advancement and retreat of the insertion portion.

7. The rotating self-traveling endoscope system according to claim 1, further comprising a housing case adapted to house the insertion portion between the rotating driving device and the flexible tube.

8. The rotating self-traveling endoscope system according to claim 7, wherein the protecting member is connected to the housing case.

* * * * *